(12) United States Patent
Zheng et al.

(10) Patent No.: US 12,121,897 B2
(45) Date of Patent: Oct. 22, 2024

(54) MICROFLUIDIC SYSTEM AND OPERATION METHOD THEREOF

(71) Applicant: SHENZHEN INSTITUTES OF ADVANCED TECHNOLOGY, Shenzhen (CN)

(72) Inventors: Hairong Zheng, Shenzhen (CN); Fei Li, Shenzhen (CN); Feiyan Cai, Shenzhen (CN); Long Meng, Shenzhen (CN); Yang Xiao, Shenzhen (CN); Fei Yan, Shenzhen (CN)

(73) Assignee: SHENZHEN INSTITUTES OF ADVANCED TECHNOLOGY, Shenzhen (CN)

( * ) Notice: Subject to any disclaimer, the term of this patent is extended or adjusted under 35 U.S.C. 154(b) by 381 days.

(21) Appl. No.: 16/769,103

(22) PCT Filed: Dec. 21, 2018

(86) PCT No.: PCT/CN2018/122688
§ 371 (c)(1),
(2) Date: Jun. 2, 2020

(87) PCT Pub. No.: WO2020/124558
PCT Pub. Date: Jun. 25, 2020

(65) Prior Publication Data
US 2021/0308676 A1 Oct. 7, 2021

(51) Int. Cl.
*B01L 3/00* (2006.01)
*B06B 1/06* (2006.01)
*B82Y 35/00* (2011.01)

(52) U.S. Cl.
CPC .......... *B01L 3/502753* (2013.01); *B06B 1/06* (2013.01); *B01L 2400/0409* (2013.01); *B01L 2400/0436* (2013.01); *B82Y 35/00* (2013.01)

(58) Field of Classification Search
CPC ....... B01L 3/502753; B01L 2400/0409; B01L 2400/0436; B01L 3/5082;
(Continued)

(56) References Cited

U.S. PATENT DOCUMENTS

| 8,727,071 | B2 * | 5/2014 | Berker | B32B 27/40 |
| | | | | 181/292 |
| 2012/0149126 | A1 * | 6/2012 | Wilson | C12N 13/00 |
| | | | | 436/175 |

(Continued)

FOREIGN PATENT DOCUMENTS

| CN | 101478709 A | 7/2009 |
| CN | 103864173 A | 6/2014 |

(Continued)

OTHER PUBLICATIONS

Lanoy et al (A Phononic Crystal-Based High Frequency Rheometer, Crystals, 2018, vol. 8, 195, pp. 1-7) (Year: 2018).*

(Continued)

*Primary Examiner* — Elizabeth A Robinson
*Assistant Examiner* — Jean C. Caraballo-Leon
(74) *Attorney, Agent, or Firm* — CANTOR COLBURN LLP (57) ABSTRACT

A microfluidic system, including: a container, an ultrasound transmitter assembly, and a phononic crystal plate. The container is configured to accommodate a solution containing microparticles. The ultrasound transmitter assembly is configured to transmit ultrasonic waves to the phononic crystal plate, where the ultrasonic waves have a frequency which is the same as a resonance frequency of the phononic crystal plate. The phononic crystal plate is placed in the solution, and configured to generate a local acoustic field on a surface of the phononic crystal plate under excitation of the ultrasonic waves, and induce an acoustic microstreaming (Continued)

vortex to generate an acoustic streaming shear stress on the microparticles. The phononic crystal plate defines therein cavities, the respective cavities are arranged periodically in the phononic crystal plate, and all the respective cavities are filled with gas.

11 Claims, 6 Drawing Sheets

(58) Field of Classification Search
CPC ..... B01L 2200/0647; B01L 2400/0439; B01L 3/5027; B01L 3/502715; B06B 1/06; B82Y 35/00; C12M 23/16; C12M 27/16; C12M 1/42; B01J 2219/00788; B01J 2219/00932; B01J 19/0093; B01J 19/10
See application file for complete search history.

(56) References Cited

U.S. PATENT DOCUMENTS

2013/0192958 A1 8/2013 Ding et al.
2015/0037808 A1* 2/2015 Donaty ................. B01F 31/201
  435/6.19
2018/0369815 A1* 12/2018 Zheng ............... B01L 3/502715

FOREIGN PATENT DOCUMENTS

CN            105214742 A      1/2016
WO     WO-2017059604 A1 *  4/2017    ........ B01L 3/502715

OTHER PUBLICATIONS

Leroy et al. (Band gaps in bubble phononic crystals, AIP Advances, 2016, vol. 6, pp. 121604-1 to 121604-6) (Year: 2016).*
Leroy et al. (Transmission of ultrasound through a single layer of bubbles, The European Physical Journal E, 2009, vol. 29, pp. 123-130) (Year: 2009).*
Leroy et al (Design and characterization of bubble phononic crystals, Applied Physics Letters, 2009, pp. 171904-1 to 171904-3) (Year: 2009).*
International Search Report and Written Opinion for Application: PCT/CN2018/122688.

* cited by examiner

MICROFLUIDIC SYSTEM AND OPERATION METHOD THEREOF

CROSS-REFERENCE TO RELATED APPLICATIONS

This application is a U.S. National Stage of International Patent Application No. PCT/CN2018/122688 filed on Dec. 21, 2018. The aforementioned application is hereby incorporated by reference in its entirety.

TECHNICAL FIELD

The present application relates to the technical field of microfluidic control, and more particularly to a microfluidic system and an operation method thereof.

BACKGROUND

Drug delivery technique with safety and high efficiency is a core technology in various technical fields, including drug development, cancer study, multifunctional stem cell induction, and tissue engineering. Ultrasonic drug delivery technique has received extensive attention due to its advantages in safety, simplicity, non-contact, non-invasive, low cost, and universal applicability, compared with virus-mediated biological delivery technology, chemical delivery technology, microinjection method, electroporation method, laser method, and other delivery technologies.

Technical Problems

The existing ultrasonic drug delivery system typically generates ultrasonic waves by an ultrasonic generator, and induces an acoustic microstreaming vortex by a phononic crystal plate provided with bosses, so as to produce an acoustic streaming shear stress, which has sonoporation effect on cells and enhance permeability of cell membranes. However, the acoustic streaming shear stress produced by such a system is small.

Technical Solutions

One aspect of the embodiments of the present application provides a microfluidic system, comprising: a container, an ultrasound transmitter assembly, and a phononic crystal plate.

The container is configured to accommodate a solution containing microparticles.

The ultrasound transmitter assembly is configured to transmit ultrasonic waves to the phononic crystal plate, where the ultrasonic waves have a frequency which is the same as a resonance frequency of the phononic crystal plate.

The phononic crystal plate is placed in the solution, and configured to generate a local acoustic field on a surface of the phononic crystal plate under excitation of the ultrasonic waves, and induce an acoustic microstreaming vortex to generate an acoustic streaming shear stress on the microparticles.

The phononic crystal plate defines therein cavities, the respective cavities are arranged periodically in the phononic crystal plate, and all the respective cavities are filled with gas.

The present application also provides an operation method, applied to a microfluidic system, comprising: a container, an ultrasound transmitter assembly, and a phononic crystal plate. The operation method comprises:

determining the resonance frequency of the phononic crystal plate;

placing the phononic crystal plate into the container;

filling the container with the solution containing microparticles; and controlling the ultrasound transmitter assembly to emit ultrasonic waves having a frequency which is the same as the resonance frequency of the phononic crystal plate, thereby generating the local acoustic field on the surface of the phononic crystal plate under the excitation of the ultrasonic waves, inducing an acoustic microstreaming vortex, and generating the acoustic streaming shear stress on the microparticles.

Beneficial Effects

In the above embodiment, due that the medium contained in all the respective cavities of the phononic crystal plate is a gas, the local acoustic field generated on the surface of the phononic crystal plate has greater field strength, induces the acoustic microstreaming vortex with greater intensity, and generates greater acoustic streaming shear stress on the microparticles, compared with the existing microfluidic system where the acoustic microstreaming vortex is induced by a phononic crystal plate provided with bosses.

DETAILED DESCRIPTION OF THE EMBODIMENTS

In order to make the purpose, technical features, and advantages of the present application more obvious and understandable, the technical solutions provided by the embodiments of the present application will be described clearly and completely in conjunction with the drawings provided by the embodiments of the present application.

Obviously, the description is only a part of the embodiments of the present application, but not all the embodiments. Based on the embodiments provided by the present application, all other embodiments obtained by those skilled in the art without making creative efforts fall within the protection scope of the present application.

It should be noted that the microfluidic system provided by various embodiments hereinbelow can be applied to the field of ultrasonic drug delivery, but cannot be construed as any limitation to the application field of such microfluidic system. The shear stress generated by the acoustic microstreaming vortex on cells can reversibly enhance the permeability of cell membrane, thereby achieving large scale ultrasonic drug delivery. The microfluidic system may also be applied to utilize the acoustic radiation force produced by a local acoustic field on a surface of a phononic crystal plate to achieve aggregation of microparticles, and to utilize an acoustic streaming shear stress imposed on microparticles by the acoustic microstreaming vortex induced by the local acoustic field to achieve the perforation of the microparticles.

Figure 1:
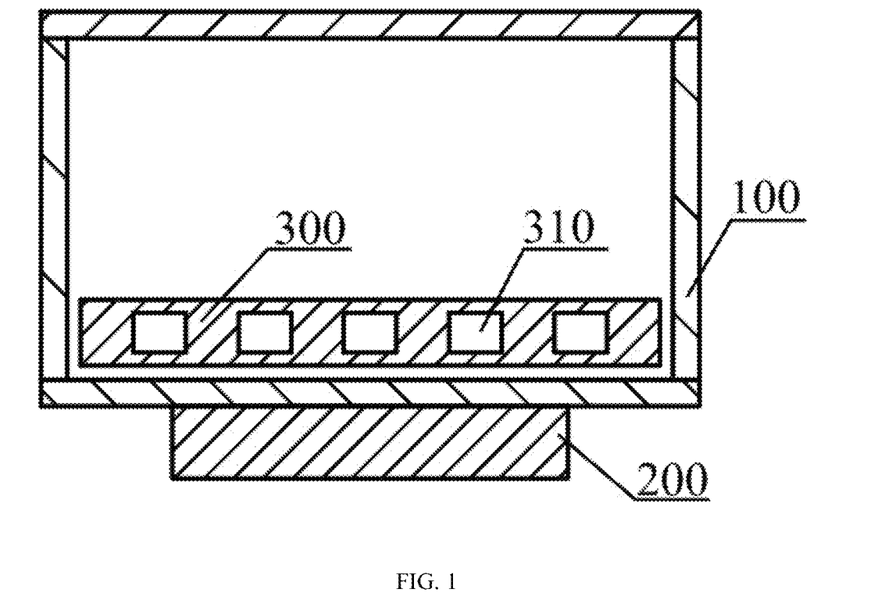
FIG. 1 is a cross-sectional view of a microfluidic system provided by a first embodiment of the present application.

Referring to FIG. 1, which is a cross-sectional view of a microfluidic system provided by a first embodiment of the present application. As shown in FIG. 1, the microfluidic system comprises: a container 100, an ultrasound transmitter assembly 200, and a phononic crystal plate 300.

The container 100 is configured to accommodate a solution containing microparticles.

The ultrasound transmitter assembly 200 is configured to transmit ultrasonic waves to the phononic crystal plate 300, where the ultrasonic waves have a frequency which is the same as a resonance frequency of the phononic crystal plate 300.

The phononic crystal plate 300 is placed in the solution within the container 100, and configured to generate a local acoustic field, and induce an acoustic microstreaming vortex to generate an acoustic streaming shear stress on the microparticles in the solution, under excitation of the ultrasonic waves.

The phononic crystal plate 300 defines therein cavities 320, the respective cavities are arranged periodically in the phononic crystal plate 300, and all the respective cavities 310 are filled with gas.

The phononic crystal is a material or structure in which an elastic constant and density are periodically distributed, and the cavities are periodically distributed in a matrix material of the phononic crystal plate 300, thereby forming the phononic crystal.

It should be noted that FIG. 1 only takes the ultrasound transmitter assembly 200 contacting the container 100 as an example for illustration, rather than limiting the positional relationship between the ultrasound transmitter assembly 200 and the container. The ultrasound transmitter assembly 200 may also be aligned with, but not contact, the container, or alternatively, the ultrasound transmitter assembly 200 may also be placed in the container 100 so that the ultrasonic waves directly act on the phononic crystal plate 300.

The existing acoustic microfluidic vortex system adopts a phononic crystal plate provided with bosses in order to induce a local field, in which, the solution in the container would fill the space between the bosses, that is, an inlay material of the phononic crystal plate provided with the bosses is a fluid, in contrast, the cavities 310 defined in the phononic crystal plate 300 which is adopted by the acoustic microstreaming vortex system of the present embodiment are filled with gas, that is, the inlay material for the phononic crystal plate 300 of the microfluidic system is the gas. On the one hand, compared with the phononic crystal plate provided with the bosses in the existing microfluidic system, a density ratio of the matrix material to the inlay material in the phononic crystal plate 300 of the microfluidic system provided by the present embodiment is greater, which is conducive to the generation of complete phononic band gaps in the phononic crystal plate 300. When the frequency of the ultrasonic waves equals to the resonance frequency of the phononic crystal plate 300, the ultrasonic waves are unable to propagate in the phononic crystal plate 300 in any directions. In such condition, the local acoustic field generated on the surface of the phononic crystal plate 300 has greater field strength. On the other hand, when being applied with the same forces, the volume variation of the gas is much greater than the volume variation of the liquid, thus, compared with the phononic crystal plate provided with the bosses in the existing microfluidic system, the phononic crystal plate 300 in the microfluidic system provided by the present embodiment produces much stronger vibration under the excitation of the ultrasonic waves, and the local acoustic field generated on the surface of the phononic crystal plate 300 has much greater field strength.

In summary, under the excitation of the ultrasonic wave, the phononic crystal plate in the microfluidic system provided by the present embodiment, compared with the phononic crystal plate provided with the bosses in the existing microfluidic system, produces the local acoustic field with much greater field strength on the surface of the phononic crystal plate 300, induces stronger acoustic microstreaming vortex, and produces stronger acoustic streaming shear stress on the microparticles.

It should be noted that the shear modulus of the matrix material of the phononic crystal plate 300 is much smaller than a longitudinal wave modulus of such material.

When the microfluidic system provided by the present embodiment is applied to the field of ultrasonic drug delivery, which means the microparticles in the solution are cells, the microfluidic system provided by the present application may produce greater acoustic streaming shear stress on the cell membranes, which makes the cell membranes have greater permeability and therefore enables the drug particles to enters cells more easily. Moreover, due that the acoustic streaming shear stress of the microfluidic system may be adjusted in a precise quantitative manner via the power of the ultrasonic waves, the arrangement, the shapes, and the gas density of the cavities of the phononic crystal plate 300, as well as the density of the matrix material of the phononic crystal plate 300, it is ensured that the acoustic streaming shear stress will not damage the cells, thereby preventing the cells from death.

In the present embodiment, due that the medium contained in all the respective cavities of the phononic crystal plate is a gas, the local acoustic field generated on the surface of the phononic crystal plate has greater field strength, induces the acoustic microstreaming vortex with greater intensity, and generates greater acoustic streaming shear stress on the microparticles, compared with the existing microfluidic system where the acoustic microstreaming vortex is induced by a phononic crystal plate provided with bosses.

Figure 2:
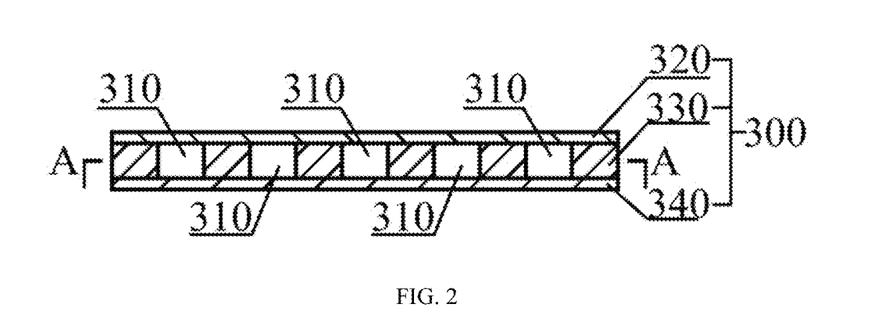
FIG. 2 is a cross-sectional view of a phononic crystal plate in a microfluidic system provided by a second embodiment of the present application.

Referring to FIG. 2, which is a cross-sectional view of a phononic crystal plate in the microfluidic system provided according to the second embodiment of the present application, as shown in FIG. 2, the present embodiment is different from the microfluidic system shown in FIG. 1 in that:

Further, the respective cavities 310 are all column cavities.

Axial directions of the respective cavities 310 are in parallel to a longitudinal wave direction of the ultrasonic waves, or alternatively, the axial directions of the respective cavities 310 are perpendicular to the longitudinal wave direction of the ultrasonic waves.

For facilitating the description, the present embodiment only takes the longitudinal wave direction of the ultrasonic waves being perpendicular to a lengthwise-widthwise surface of the phononic crystal plate 300 as an example for illustration, however, according to different relative positions between the ultrasound transmitter assembly 200 and the phononic crystal plate 300, the longitudinal wave direction of the ultrasonic waves may be other directions.

FIG. 2 only takes the longitudinal wave direction of each cavity 310 parallel to the longitudinal wave direction of ultrasonic waves as an example to illustrate the axial direction of each cavity 310, and is not intended to restrict the axial direction of each cavity 310. The axis direction of each cavity 310 may also be perpendicular to the longitudinal wave direction of ultrasonic waves.

Figure 3:
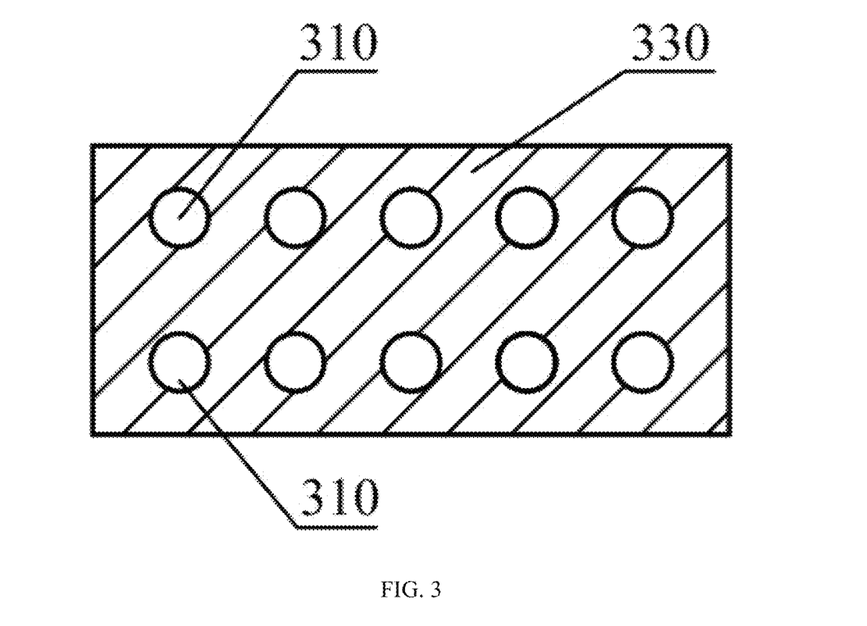
FIG. 3 is a cross-sectional view taken from line A-A of the phononic crystal plate of FIG. 2.

As shown in FIG. 3, which is a cross-sectional view taken from line A-A of the phononic crystal plate of FIG. 2, in a plane perpendicular to the axial directions of the respective cavities 310, cross-sectional shapes of the respective cavities 310 are the same. It should be understood that FIG. 3 only takes the cross-sectional shapes of the respective cavities 310 in a plane perpendicular to the axial directions of the respective cavities 310 being circular as an example for illustration, rather than restricting the cross-sectional shapes of the respective cavities 310 in the plane perpendicular to the axes of the respective cavities, the cross-section shapes of the respective cavities 310 in such cross section may also be elliptical or polygonal.

Further, as shown in FIG. 2, the phononic crystal plate 300 comprises: a first plate 320, a second plate 330, and a third plate 340.

Figure 4:
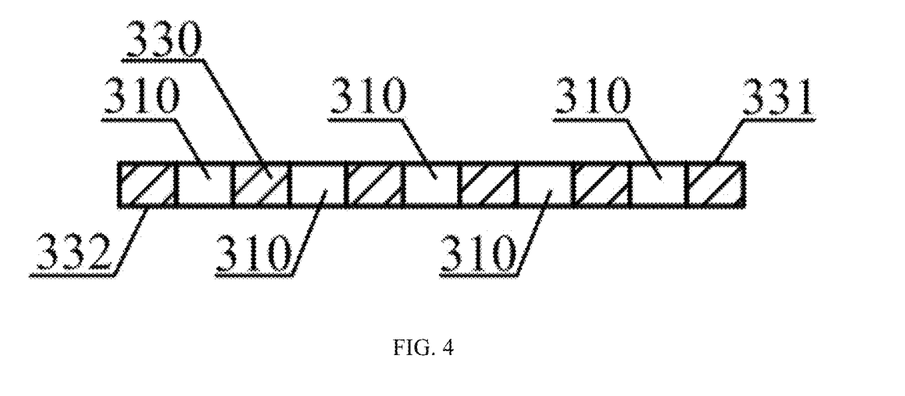
FIG. 4 is a cross-sectional view of a second plate in the microfluidic system provided by the second embodiment of the present application.
Figure 5:
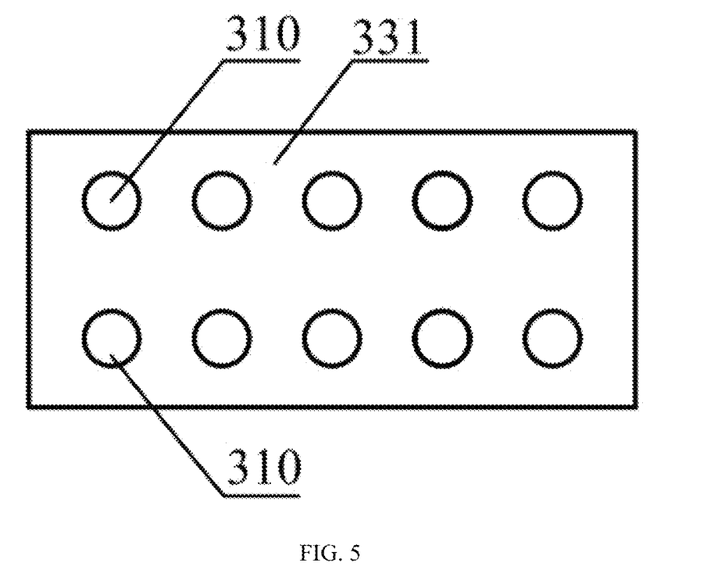
FIG. 5 is a top view of the second plate in the microfluidic system provided by the second embodiment of the present application.
Figure 6:
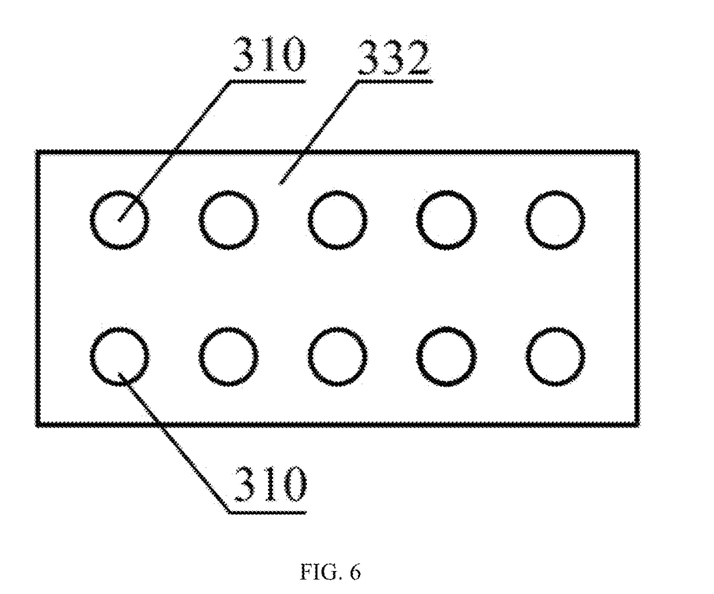
FIG. 6 is a bottom view of the second plate in the microfluidic system provided by the second embodiment of the present application.

Referring to FIGS. 4 to 6, in which, FIG. 4 is a cross-sectional view of the second plate in the microfluidic system provided by the second embodiment of the present application, and FIG. 5 is a top view of the second plate in the microfluidic system provided by the second embodiment of the present application, and FIG. 6 is a bottom view of the second plate in the microfluidic system provided by the second embodiment of the present application. In combination with FIGS. 4-6, the second plate 330 comprises a first surface 331 and a second surface 332 opposite to the first surface 331, the cavities 310 are periodically arranged in the second plate 330, and the respective cavities 310 all penetrate through the first surface 331 and the second surface 332.

In combination with FIG. 2, and FIGS. 4-6, the first plate 320 and the third plate 340 are respectively fixed to the first surface 331 and the second surface 332 of the second plate 330, respectively.

It should be noted that the second plate 330 is processed to form through holes periodically arranged therein, and then the first plate 320 and the third plate 340 are fixed on the first surface 331 and the second surface 332, respectively, to seal the air in the cavities 310. In this way, the fabrication of the phononic crystal plate 300 is simple.

Optionally, the first plate 320 and the third plate 340 may be fixed to the first surface 331 and the second surface 332, respectively, after filling the cavities with a gas having a specific density, to seal the gas having the specific density within the respective cavities, such that the resonance frequency of the phononic crystal plate 300 can be adjusted, the field strength and the distribution of the local acoustic field generated on the surface of the phononic crystal plate 300 can be adjusted under the excitation of the ultrasonic waves, and in turn the acoustic streaming shear stress can be adjusted.

Further, the first plate 320, the second plate 330, and the third plate 340 are all made from a poly dimethylsiloxane, and the first plate 320, the second plate 330, and the third plate 340 are all flexible plates.

Both the first plate 320 and the third plate 340 are in connection with the second plate 330 via bonding.

It should be noted that, since the first plate 320, the second plate 330, and the third plate 340 are all made from a polydimethylsiloxane having biocompatibility, thus, when the microfluidic system provided by the present application is applied to the field of ultrasonic drug delivery, the phononic crystal plate 300 is prevented from damaging the cells.

In practical applications, noise may be generated in the phononic crystal plate 300 under the influence of external factors, the frequency of the noise is not equal to the resonance frequency of the phononic crystal plate 300, and the frequency of the noise is not within the band of the phononic crystal plate 300, therefore, the noise can propagate in the phononic crystal plate 300 and affect the local acoustic field of the phononic crystal plate 300, which is not conducive to the precise control of the acoustic streaming shear stress. Since the first plate 320, the second plate 330, and the third plate 340 are all flexible plates, the noise can be buffered and absorbed, in this way, the noise is prevented from adversely affecting the precise control of the acoustic streaming shear stress.

Figure 7:
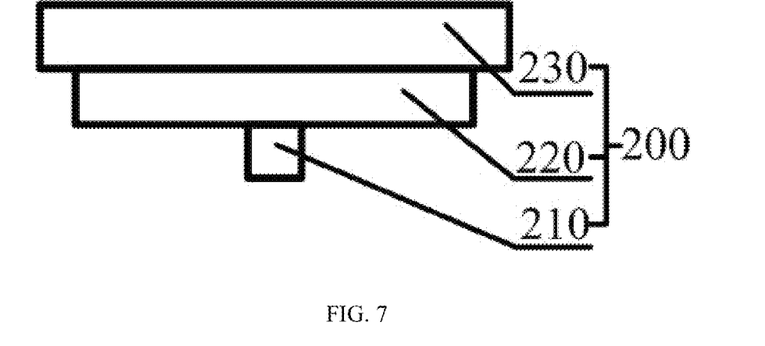
FIG. 7 is a structural view of an ultrasound transmitter assembly in the microfluidic system provided by the second embodiment of the present application.

Further, as shown in FIG. 7, which is a structural view of an ultrasound transmitter assembly in the microfluidic system provided by the second embodiment of the present application. As shown in FIG. 7, the ultrasound transmitter assembly 200 comprises: a signal generator 210, a power amplifier 220, and an ultrasonic transducer 230.

The signal generator 210 is configured to transmit a driver signal.

The power amplifier 220 is in connection with the signal generator 210, and configured for amplifying the driver signal.

The ultrasonic transducer 230 is in connection with the power amplifier 220, and configured to emit the ultrasonic waves corresponding to a frequency of the driver signal under the excitation of the amplified driver signal.

Further, the signal generator 210 is a programming signal transmitter.

The power amplifier 220 is a linear power amplifier.

The ultrasonic transducer 230 is a single-array element ultrasonic transducer, a phased array ultrasonic transducer, a linear array ultrasonic transducer, a convex array ultrasonic transducer, or an interdigital transducer.

A transmission signal of the signal generator 210 may be a continuous sinusoidal signal or a pulsed sinusoidal signal.

Optionally, the phononic crystal plate 300 can be fixed in the container through a friction between the phononic crystal plate 300 and the container 100. A support platform may also be provided in the container 100 to support the phononic crystal plate 300, such that the phononic crystal plate 300 is separated from the ultrasonic transducer 230 with a preset distance.

In this embodiment, in a first aspect, since the medium contained in the respective cavities of the phononic crystal plate is a gas, the local acoustic field generated on the surface of the phononic crystal plate has greater field strength, induces the acoustic microstreaming vortex with greater intensity, and generates greater acoustic streaming shear stress on the microparticles, compared with the existing microfluidic system where the acoustic microstreaming vortex is induced by a phononic crystal plate provided with bosses. In a second aspect, the respective cavities in the phononic crystal plate have flexible arrangements and variable cross-sectional shapes, thus the acoustic streaming shear stress can be precisely adjusted within a greater range. In a third aspect, the phonon crystal plate comprises: the first plate, the second plate, and the third plate: the second plate is processed to form through holes therein, the first plate and the third plate are then connected to the second plate to seal two open ends of each through hole, in this way, the phononic crystal plate having bubble cavities are obtained, and the fabrication of such phononic crystal plate is simple. In a fourth aspect, due that the first plate, the second plate, and the third plate are all flexible plates that can buffer and absorb the noises generated by external factors, thus preventing the noise from adversely affecting the precise control of the precise control of the acoustic streaming shear stress.

Figure 8:
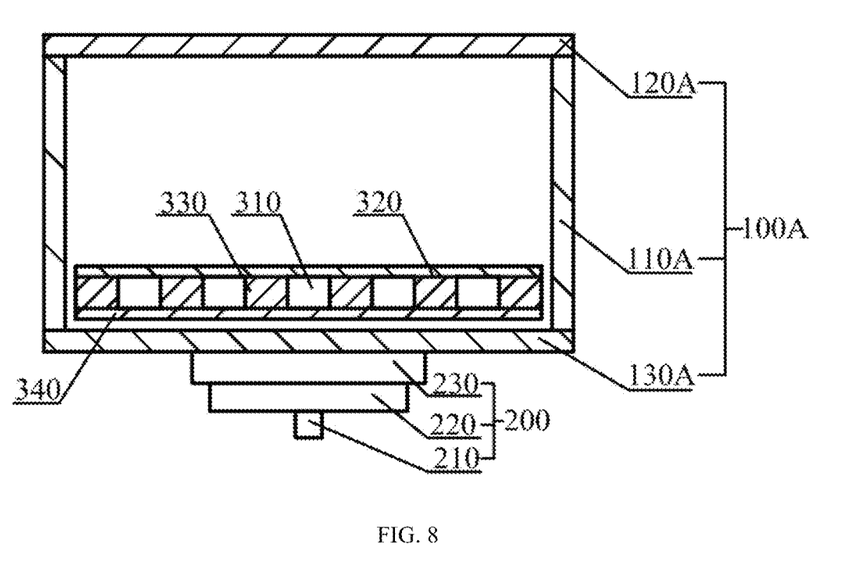
FIG. 8 is a cross-sectional view of a microfluidic system provided by a third embodiment of the present application.

As shown in FIG. 8, which is a cross-section view of a microfluidic system provided by a third embodiment of the present application. The embodiment as illustrated in FIG. 8 is different from the microfluidic systems shown in FIGS. 1-7 in that:

Further, the container 100 is a microcavity 100A.

The ultrasonic transducer 230 contacts with the microcavity 100A.

Further, as shown in FIG. 8, the microcavity 100A comprises: a microcavity body 110A, a top plate 120A, and a bottom plate 130A.

The microcavity body 110A is made from a polydimethylsiloxane, and the top plate 120A and the bottom plate 130A are made of a quartz glass, an organic glass, a silicon wafer, or lithium niobate.

The microcavity body 110A is a hollow tube, and the microcavity body 110A comprises two opposite open ends.

The top plate 120A and the bottom plate 130A are respectively fixed to the two opposite open ends by bonding.

The ultrasonic transducer 230 is in contact with the microcavity 100A, and the microcavity 100A vibrates under the excitation of ultrasonic waves and transmits the vibration to the phononic crystal plate 300.

In this embodiment, in a first aspect, since the medium contained in the respective cavities of the phononic crystal plate is a gas, the local acoustic field generated on the surface of the phononic crystal plate has greater field strength, induces the acoustic microstreaming vortex with greater intensity, and generates greater acoustic streaming shear stress on the microparticles, compared with the existing microfluidic system where the acoustic microstreaming vortex is induced by a phononic crystal plate provided with bosses. In a second aspect, the respective cavities in the phononic crystal plate have flexible arrangements and variable cross-sectional shapes, thus the acoustic streaming shear stress can be precisely adjusted within a greater range. In a third aspect, the phononic crystal plate comprises: the first plate, the second plate, and the third plate: the second plate is processed to form through holes therein, the first plate and the third plate are then connected to the second plate to seal two open ends of each through hole, in this way, the phononic crystal plate having bubble cavities are obtained, and the fabrication of such phononic crystal plate is simple. In a fourth aspect, due that the first plate, the second plate, and the third plate are all flexible plates that can buffer and absorb the noises generated by external factors, thus preventing the noise from adversely affecting the precise control of the precise control of the acoustic streaming shear stress. In a fifth aspect, due that the ultrasonic waves are transmitted to the phononic crystal plate by the microcavity, the microcavity does not require any processing, and the structure thereof is simple.

Figure 9:
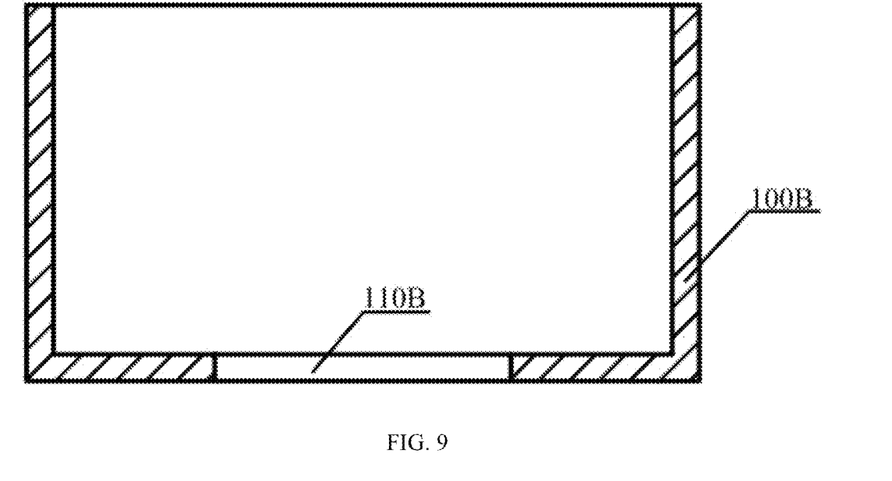
FIG. 9 is a cross-sectional view of a container of a microfluidic system provided by a fourth embodiment of the present application.
Figure 10:
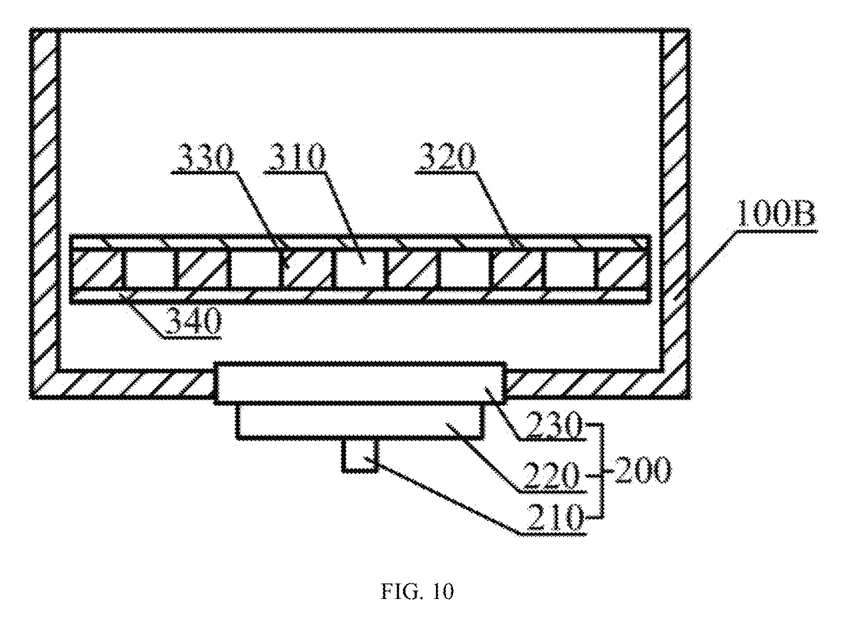
FIG. 10 is a cross-sectional view showing the container in the microfluidic system provided by the fourth embodiment of the present application.

Referring to FIGS. 9-10, in which, FIG. 9 is a cross-sectional view of a container in the microfluidic system provided by the fourth embodiment of the present application, and FIG. 10 is a cross-sectional view showing the container in the microfluidic system provided by the fourth embodiment of the present application. The present embodiment, in combination with FIGS. 9-10, is different from those illustrated in FIGS. 1-7 in that:

Further, the container 100 is a box 100B, and an opening 110B is defined in the bottom face of the box 100B.

The ultrasonic transducer 230 is arranged within the opening 110B, and the ultrasonic transducer 230 and the opening 110B are in an interference fit.

Optionally, the ultrasonic transducer 230 and the opening 110B are in clearance fit or transition fit, and a waterproof glue is provided between the ultrasonic transducer 230 and an inner wall of the opening 110B to fix the ultrasonic transducer 230 in the opening 110B, as well as preventing the solution containing microparticles from leaking out via the opening 110B.

In this embodiment, in a first aspect, since the medium contained in the respective cavities of the phononic crystal plate is a gas, the local acoustic field generated on the surface of the phononic crystal plate has greater field strength, induces the acoustic microstreaming vortex with greater intensity, and generates greater acoustic streaming shear stress on the microparticles, compared with the existing microfluidic system where the acoustic microstreaming vortex is induced by a phononic crystal plate provided with bosses. In a second aspect, the respective cavities in the phononic crystal plate have flexible arrangements and variable cross-sectional shapes, thus the acoustic streaming shear stress can be precisely adjusted within a greater range. In a third aspect, the phononic crystal plate comprises: the first plate, the second plate, and the third plate: the second plate is processed to form through holes therein, the first plate and the third plate are then connected to the second plate to seal two open ends of each through hole, in this way, the phononic crystal plate having bubble cavities are obtained, and the fabrication of such phononic crystal plate is simple. In a fourth aspect, due that the first plate, the second plate, and the third plate are all flexible plates that can buffer and absorb the noises generated by external factors, thus preventing the noise from adversely affecting the precise control of the precise control of the acoustic streaming shear stress. In a fifth aspect, because the ultrasonic transducer is arranged within the opening, the ultrasonic waves can directly act on the phononic crystal plate, which reduces the propagation loss, and further improves the acoustic streaming shear stress.

Figure 11:
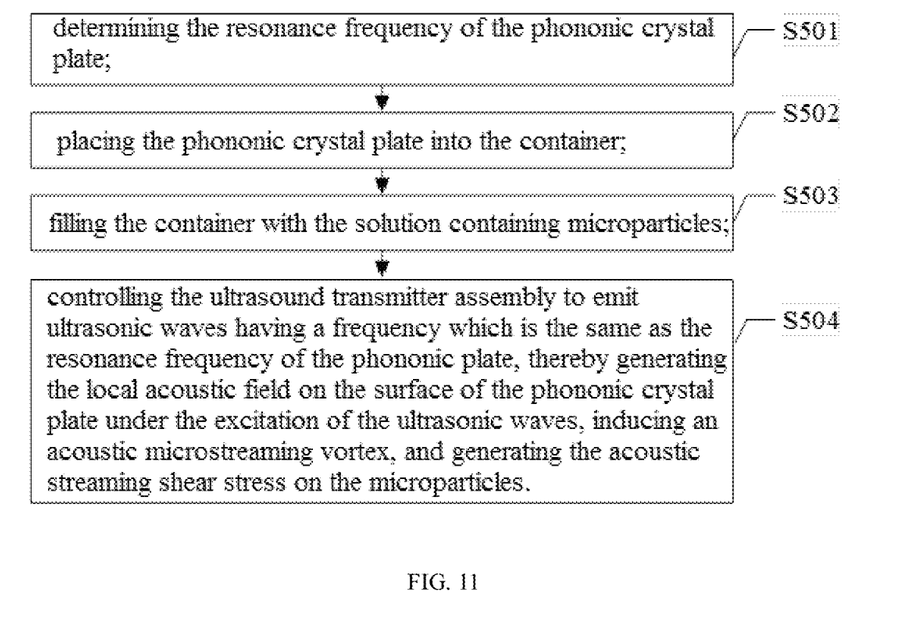
FIG. 11 is a flow chart of an operation method provided by a fifth embodiment of the present application.

Referring to FIG. 11, which is a flowchart of an operation method provided by a fifth embodiment of the present application. The operation method is applied to a microfluidic system comprising:

a container, an ultrasound transmitter assembly, and a phononic crystal plate.

As shown in FIG. 11, the method comprises:

S501: determining the resonance frequency of the phononic crystal plate;

In particular, according to a geometric dimension and material parameters of the phononic crystal plate, the frequency band to be tested where the resonance frequency of the phononic crystal plate is located is obtained through theoretical calculation.

The resonance frequency of the phononic crystal plate within the frequency band to be tested is obtained by experiment. The experiment may be performed as follows, for example, placing the phononic crystal plate in water, and changing a step at a preset frequency within the frequency band to be tested, and the phononic crystal plate is excited by different frequencies to obtain a transmission spectrum of the phononic crystal plate. A frequency of an abscissa corresponding to a maximum value of an ordinate in the transmission spectrum is determined as the resonance frequency of the phononic crystal plate.

For example, the measured transmission spectrum of the phononic crystal plate has two maximum values. The maximum values correspond to the abscissa frequency of 1.547 MHz and 1.804 MHz, respectively, then the resonance frequency of the phononic crystal plate is 1.547 MHz and 1.804 MHZ.

S502: placing the phononic crystal plate into the container;

S503: filling the container with the solution containing microparticles; and

S504: controlling the ultrasound transmitter assembly to emit ultrasonic waves having a frequency which is the same as the resonance frequency of the phononic plate, thereby generating the local acoustic field on the surface of the phononic crystal plate under the excitation of the ultrasonic waves, inducing an acoustic microstreaming vortex, and generating the acoustic streaming shear stress on the microparticles.

In particular, the ultrasound transmitter assembly comprises: a signal generator, a power amplifier, and an ultrasonic transducer.

The signal generator is controlled to emit an excitation signal having a center frequency equal to the resonance frequency, the excitation signal is amplified by the power amplifier and transmitted to the ultrasonic transducer. And the ultrasonic transducer emits ultrasonic waves having a frequency equal to the resonance frequency, under the excitation of the excitation signal.

Under the excitation of the ultrasonic waves, the local acoustic field is generated on the surface of the phononic crystal plate, which generates the acoustic radiation force to capture the microparticles in the solution, and at the same time induces the acoustic microstreaming vortex to impose the acoustic streaming shear stress on the captured particles.

In practical applications, the phononic crystal plate can have multiple resonance frequencies. Under the excitation of different resonance frequencies, the phononic crystal plate will produce different vibration modes. The different vibration modes have different effects on the distribution of the local acoustic field generated on the surface of the phononic crystal plate. Thus, the acoustic streaming shear stress on the microparticles may be adjusted by selecting different resonance frequencies.

In this embodiment, since the medium contained in the respective cavities of the phononic crystal plate is a gas, the local acoustic field generated on the surface of the phononic crystal plate has greater field strength, induces the acoustic microstreaming vortex with greater intensity, and generates greater acoustic streaming shear stress on the microparticles, compared with the existing microfluidic system where the acoustic microstreaming vortex is induced by a phononic crystal plate provided with bosses.

What is claimed is:

1. A microfluidic system, comprising: a microcavity, an ultrasound transmitter assembly, and a phononic crystal plate; wherein the microcavity is configured to accommodate a solution containing microparticles;

the ultrasound transmitter assembly is configured to transmit ultrasonic waves to the phononic crystal plate, wherein the ultrasonic waves have a frequency which is the same as a resonance frequency of the phononic crystal plate, the ultrasound transmitter assembly comprises:

a signal generator, a power amplifier, and an ultrasonic transducer, and the ultrasonic transducer contacts with the microcavity;

the phononic crystal plate is placed in the solution, and configured to generate a local acoustic field on a surface of the phononic crystal plate under excitation of the ultrasonic waves, and induce an acoustic microstreaming vortex to generate an acoustic streaming shear stress on the microparticles;

the phononic crystal plate defines therein cavities, the respective cavities are arranged periodically in the phononic crystal plate, and all the respective cavities are filled with gas;

the phononic crystal plate comprises: a first plate, a second plate, and a third plate;

the second plate comprises a first surface and a second surface opposite to the first surface, the cavities are periodically arranged in the second plate, and all the cavities penetrate through the first surface and the second surface; and the first plate and the third plate are respectively fixed to the first surface and the second surface of the second plate, respectively;

the first plate, the second plate, and the third plate are all made from a polydimethylsiloxane, and the first plate, the second plate, and the third plate are all flexible plates; and both the first plate and the third plate are in connection with the second plate via bonding.

2. The microfluidic system of claim 1, wherein the respective cavities are all column cavities;

axial directions of the respective cavities are in parallel to a longitudinal wave direction of the ultrasonic waves, or alternatively, the axial directions of the respective cavities are perpendicular to the longitudinal wave direction of the ultrasonic waves; and in a plane perpendicular to the axial directions of the respective cavities, cross-sectional shapes of the respective cavities are the same, and the cross-section shapes are circles, ovals, or polygons.

3. The microfluidic system of claim 1, wherein the microcavity comprises: a microcavity body, a top plate, and a bottom plate;

the microcavity body is made from a polydimethylsiloxane, and the top plate and the bottom plate are made of a quartz glass, an organic glass, a silicon wafer, or lithium niobate;

the microcavity body is a hollow tube, and the microcavity body comprises two opposite open ends;

the top plate and the bottom plate are fixed to the two opposite open ends by bonding, respectively.

4. The microfluidic system of claim 1, wherein the phononic crystal plate has multiple resonance frequencies and is configured to produce different vibration modes under excitation of different resonance frequencies so as to adjust an acoustic streaming shear stress on the microparticles.

5. The microfluidic system of claim 1, wherein
the signal generator is configured to transmit a driver signal;
the power amplifier is in connection with the signal generator, and configured for amplifying the driver signal; and
the ultrasonic transducer is in connection with the power amplifier, and configured to emit the ultrasonic waves corresponding to a frequency of the driver signal under the excitation of the amplified driver signal.

6. The microfluidic system of claim 5, wherein
the signal generator is a programming signal transmitter;
the power amplifier is a linear power amplifier; and
the ultrasonic transducer is a single-array element ultrasonic transducer, a phased array ultrasonic transducer, a linear array ultrasonic transducer, a convex array ultrasonic transducer, or an interdigital transducer.

7. An operation method for a microfluidic system, comprising:
providing the microfluidic system, comprising: a microcavity, an ultrasound transmitter assembly, and a phononic crystal plate;
wherein
the microcavity is configured to accommodate a solution containing microparticles;
the ultrasound transmitter assembly is configured to transmit ultrasonic waves to the phononic crystal plate, wherein the ultrasonic waves have a frequency which is the same as a resonance frequency of the phononic crystal plate, the ultrasound transmitter assembly comprises:
a signal generator, a power amplifier, and an ultrasonic transducer, and the ultrasonic transducer contacts with the microcavity;
the phononic crystal plate is configured to be placed in the solution and generate a local acoustic field on a surface of the phononic crystal plate under excitation of the ultrasonic waves, and induce an acoustic microstreaming vortex to generate an acoustic streaming shear stress on the microparticles;
the phononic crystal plate defines therein cavities, the respective cavities are arranged periodically in the phononic crystal plate, and all the respective cavities are filled with gas;
the phononic crystal plate comprises: a first plate, a second plate, and a third plate;
the second plate comprises a first surface and a second surface opposite to the first surface, the cavities are periodically arranged in the second plate, and all the cavities penetrate through the first surface and the second surface;
the first plate and the third plate are respectively fixed to the first surface and the second surface of the second plate, respectively;
the first plate, the second plate, and the third plate are all made from a polydimethylsiloxane, and the first plate, the second plate, and the third plate are all flexible plates; and
both the first plate and the third plate are in connection with the second plate via bonding;
determining the resonance frequency of the phononic crystal plate;
placing the phononic crystal plate into the microcavity;
filling the microcavity with the solution containing microparticles; and controlling the ultrasound transmitter assembly to emit ultrasonic waves having a frequency which is the same as the resonance frequency of the phononic plate, thereby generating the local acoustic field on the surface of the phononic crystal plate under the excitation of the ultrasonic waves, inducing an acoustic microstreaming vortex, and generating the acoustic streaming shear stress on the microparticles.

8. The operation method of claim 7, wherein the respective cavities are all column cavities;
axial directions of the respective cavities are in parallel to a longitudinal wave direction of the ultrasonic waves, or alternatively, the axial directions of the respective cavities are perpendicular to the longitudinal wave direction of the ultrasonic waves; and in a plane perpendicular to the axial directions of the respective cavities, cross-sectional shapes of the respective cavities are the same, and the cross-section shapes are circles, ovals, or polygons.

9. The operation method of claim 7, wherein
the microcavity comprises: a microcavity body, a top plate, and a bottom plate;
the microcavity body is made from a polydimethylsiloxane, and the top plate and the bottom plate are made of a quartz glass, an organic glass, a silicon wafer, or lithium niobate;
the microcavity body is a hollow tube, and the microcavity body comprises two opposite open ends;
the top plate and the bottom plate are fixed to the two opposite open ends by bonding, respectively.

10. The operation method of claim 7, wherein
the signal generator is configured to transmit a driver signal;
the power amplifier is in connection with the signal generator, and configured for amplifying the driver signal; and
the ultrasonic transducer is in connection with the power amplifier, and configured to emit the ultrasonic waves corresponding to a frequency of the driver signal under the excitation of the amplified driver signal.

11. The operation method of claim 10, wherein
the signal generator is a programming signal transmitter;
the power amplifier is a linear power amplifier; and
the ultrasonic transducer is a single-array element ultrasonic transducer, a phased array ultrasonic transducer, a linear array ultrasonic transducer, a convex array ultrasonic transducer, or an interdigital transducer.

\* \* \* \* \*